(12) United States Patent
Ronda et al.

(10) Patent No.: US 9,958,554 B2
(45) Date of Patent: May 1, 2018

(54) DETECTION APPARATUS FOR DETECTING RADIATION

(71) Applicant: KONINKLIJKE PHILIPS N.V., Eindhoven (NL)

(72) Inventors: Cornelis Reinder Ronda, Aachen (DE); Roland Proksa, Neu Wulmstorf (DE); Axel Thran, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 703 days.

(21) Appl. No.: 14/359,337

(22) PCT Filed: Nov. 23, 2012

(86) PCT No.: PCT/IB2012/056684
§ 371 (c)(1),
(2) Date: May 20, 2014

(87) PCT Pub. No.: WO2013/084106
PCT Pub. Date: Jun. 13, 2013

(65) Prior Publication Data
US 2014/0321617 A1 Oct. 30, 2014

Related U.S. Application Data

(60) Provisional application No. 61/566,752, filed on Dec. 5, 2011.

(51) Int. Cl.
*G01T 1/20* (2006.01)
*G01T 1/202* (2006.01)
*G01N 23/04* (2018.01)

(52) U.S. Cl.
CPC .......... *G01T 1/2002* (2013.01); *G01N 23/04* (2013.01); *G01T 1/202* (2013.01); *G01T 1/2006* (2013.01); *G01T 1/2018* (2013.01)

(58) Field of Classification Search
CPC .... G01T 1/2018; G01T 1/2002; G01T 1/2006
See application file for complete search history.

(56) References Cited

U.S. PATENT DOCUMENTS 7,138,633 B1 11/2006 Rozsa et al.
7,388,208 B2 6/2008 Deych
(Continued)

FOREIGN PATENT DOCUMENTS

JP 5045468 2/1993
JP 9152485 6/1997
(Continued)

OTHER PUBLICATIONS

"An array of Fabry-Perot optical-channels for biological fluids analysis", Sensors and Actuators A 115 (2004) 362-367, to Minas et al.*

(Continued)

*Primary Examiner* — Kenneth J Malkowski

(57) ABSTRACT

The invention relates to a detection apparatus for detecting radiation. The detection apparatus comprises a GOS material (20) for generating scintillation light depending on the detected radiation (25), an optical filter (24) for reducing the intensity of a part of the scintillation light having a wavelength being larger than 650 nm, and a detection unit (21) for detecting the filtered scintillation light. Because of the filtering procedure relatively slow components, i.e. components corresponding to a relatively large decay time, of the scintillation light weakly constribute to the detection process or are not detected at all by the detection unit, thereby increasing the temporal resolution of the detection apparatus. The resulting fast detection apparatus can be suitable for kVp-switching computed tomography systems.

14 Claims, 5 Drawing Sheets

(56) References Cited

U.S. PATENT DOCUMENTS

| | | |
|---|---|---|
| 2001/0024274 A1 | 9/2001 | Shimizu et al. |
| 2010/0072376 A1 | 3/2010 | Ronda |
| 2011/0085719 A1 | 4/2011 | Fan et al. |

FOREIGN PATENT DOCUMENTS

| | | |
|---|---|---|
| WO | 1995023348 | 8/1995 |
| WO | 2010015955 A2 | 2/2010 |

OTHER PUBLICATIONS

Alvarez, R. E., et al.; Energy-selective Reconstructions in X-ray Computerized Tomography; 1976; Phys. Med. Biol.; 21(5)733-744.
Satoh, N., et al.; High-luminance flourescent screen with interference filter; 1995; Proc. of SPIE; 2432:462-469.

* cited by examiner

DETECTION APPARATUS FOR DETECTING RADIATION

CROSS REFERENCE TO RELATED APPLICATIONS

This application is a national filing of PCT application Serial No. PCT/IB2012/056684, filed Nov. 23, 2012, published as WO 2013/084106 A2 on Jun. 13, 2013, which claims the benefit of U.S. provisional application Ser. No. 61/566,752 filed Dec. 5, 2011, which is incorporated herein by reference.

FIELD OF THE INVENTION

The invention relates to a detection apparatus and a detection method for detecting radiation. The invention relates further to an imaging system and an imaging method for imaging an object.

BACKGROUND OF THE INVENTION

US 2011/0085719 A1 discloses a computed tomography system including a generator configured to energize an x-ray source to a first kilovoltage (kVp) and to a second kVp. The computed tomography system further comprises a computer that is programmed to acquire a first view dataset with the x-ray source energized to the first kVp and a second view dataset with the x-ray source energized to the second kVp, and to reconstruct a pair of base material images from the first view dataset and from the second view dataset. For acquiring the first view dataset and the second view dataset the computed tomography system comprises a detector assembly with scintillator arrays and corresponding photodiode arrays. The scintillator arrays generate scintillation light depending on x-rays traversing the scintillator arrays, and the photodiode array detects the generated scintillation light. The quality of the first view dataset and the second view dataset can be reduced due to a limited temporal resolution of the detector assembly, which may not be sufficient for accurately following a switching between the first kVp and the second kVp.

SUMMARY OF THE INVENTION

It is an object of the present invention to provide a detection apparatus and a detection method for detecting radiation, wherein the quality of detecting the radiation can be improved. It is a further object of the present invention to provide an imaging system and an imaging method for imaging an object using the improved radiation detection.

In a first aspect of the present invention a detection apparatus for detecting radiation is presented, wherein the detection apparatus comprises:
  a GOS material for generating scintillation light depending on the detected radiation,
  an optical filter for reducing the intensity of a part of the scintillation light having a wavelength being larger than 650 nm,
  a detection unit for detecting the filtered scintillation light.

Since a GOS material is used for generating the scintillation light depending on the detected radiation, wherein an optical filter filters the scintillation light such that the intensity of scintillation light having a wavelength being larger than 650 nm is reduced, before the scintillation light is detected, relatively slow components, i.e. components corresponding to a relatively large decay time, of the scintillation light weakly constribute to the detection process or are not detected at all by the detection unit, thereby increasing the temporal resolution of the detection apparatus.

The GOS material is a gadolinium oxysulfide material, which may be doped with, for instance, Pr and/or Ce, and the detection unit is preferentially a photodiode.

The detection apparatus can comprise a one- or two-dimensional GOS material array and a corresponding one- or two-dimensional array of photodiodes for providing a one- or two-dimensional detection apparatus.

Preferentially, the optical filter is adapted to block the intensity of scintillation light having a wavelength being larger than 650 nm. In a preferred embodiment, the optical filter is arranged between the GOS material and the detection unit. This allows the optical filter to very effectively reduce the intensity of scintillation light having a wavelength being larger than 650 nm. In particular, scintillation light having a wavelength being larger than 650 nm can effectively be blocked from being detected by the detection unit.

It is further preferred that the optical filter is a band pass filter being adapted such that scintillation light having a wavelength within a range of 450 and 650 nm is transmitted by the optical filter. Thus, only a part of the scintillation light corresponding to transitions having a relatively small decay time constant reaches the detection unit, thereby further increasing the temporal resolution of the detection apparatus.

The optical filter is, for example, an optical absorption filter or an interference filter. If the optical filter is an interference filter, the scintillation light having a wavelength being larger than 650 nm is not necessarily completely lost. For instance, the scintillation light having a wavelength being larger than 650 nm can be directed to another detection unit for detecting also this light.

In an embodiment, the optical filter is reflective to scintillation light having a wavelength being smaller than 650 nm and adapted to absorb light having a wavelength being larger than 650 nm, wherein the optical filter is arranged such that the scintillation light is reflected into the GOS material. In particular, the detection apparatus can comprise an array of detection pixels, wherein each pixel comprises the GOS material and the detection unit, wherein the optical filter is arranged on a surface of the GOS material not facing the detection unit. For instance, the GOS material can comprise a radiation entering surface, a scintillation light leaving surface facing the detection unit and side surfaces connecting the radiation entering surface and the scintillation light leaving surface, wherein the optical filter is arranged on at least one of the radiation entering and side surfaces. In an embodiment, the optical filter is arranged on the radiation entering surface and all side surfaces.

Since the optical filter can be arranged on the radiation entering surface and/or the side surfaces, wherein the optical filter can be adapted to reflect scintillation light having a wavelength being smaller than 650 nm, the optical filter can fulfill two functions: reducing the part of the scintillation light having a wavelength being larger than 650 nm and preventing scintillation light from being lost, in particular, from being detected by possible neighbouring detection pixels.

The optical filter can be a non-scattering filter or a scattering filter. If the optical filter is arranged between the GOS material and the detection unit, the optical filter is preferentially a non-scattering filter. The non-scattering filter can be an interference filter or a non-scattering absorption filter, which can be realized, for example, by applying thin films of organic dyes dispersed in a polymer or a resin. If the optical filter is arranged such that the scintillation light does not pass through the optical filter before being detected by the detection unit, for example, because the optical filter is arranged on the side surfaces and optionally the radiation entering surface, the optical filter is preferentially a scattering or non-scattering optical absorption filter.

In a further aspect of the present invention an imaging system for imaging an object is presented, wherein the imaging system comprises:
  a radiation source for generating radiation for traversing the object,
  a detection apparatus for detecting the radiation, after having traversed the object, as defined in claim 1 for generating an image of the object.

It is preferred that the imaging system further comprises a reconstruction unit for reconstructing an image of the object based on the detected radiation. However, the detection apparatus itself can also be adapted to generate an image of the object being, for instance, a projection image of the object.

The imaging system is preferentially a computed tomography imaging system with kVp switching, wherein alternatingly x-ray pulses having different mean x-ray energies are generated. Correspondingly, the detection apparatus is preferentially adapted to generate detection values, which correspond to the different x-ray mean energies, i.e. the combination of a kVp-switching x-ray source and of the detection apparatus allows the imaging system to generate energy-resolved detection values. The reconstruction unit is preferentially adapted to generate an image of the object based on these energy-resolved detection values. In particular, the reconstruction unit can be adapted to decompose the energy-resolved detection values into different component detection values which correspond to different components, for instance, different physical effects like the Compton effect or the photoelectric effect, or which correspond to different materials like iodine, bone, soft tissue et cetera. The reconstruction unit can be adapted to reconstruct corresponding component images by using a computed tomography reconstruction algorithm like a filtered back protection or a Radon inversion.

In a further aspect of the present invention a detection method for detecting radiation is presented, wherein the detection method comprises:
  generating scintillation light depending on the detected radiation by a GOS material,
  reducing the intensity of a part of the scintillation light having a wavelength being larger than 650 nm by an optical filter,
  detecting the filtered scintillation light by a detection unit.

In a further aspect of the present invention an imaging method for imaging an object is presented, wherein the imaging method comprises:
  generating radiation for traversing the object by a radiation source,
  detecting the radiation, after having traversed the object, as defined in claim 14, for generating an image of the object.

It shall be understood that the detection apparatus of claim 1, the imaging system of claim 12, the detection method of claim 14, and the imaging method of claim 15 have similar and/or identical preferred embodiments as defined in the dependent claims.

It shall be understood that a preferred embodiment of the invention can also be any combination of the dependent claims with the respective independent claims.

These and other aspects of the invention will be apparent from and elucidated with reference to the embodiments described hereinafter.

DETAILED DESCRIPTION OF EMBODIMENTS

Figure 1:
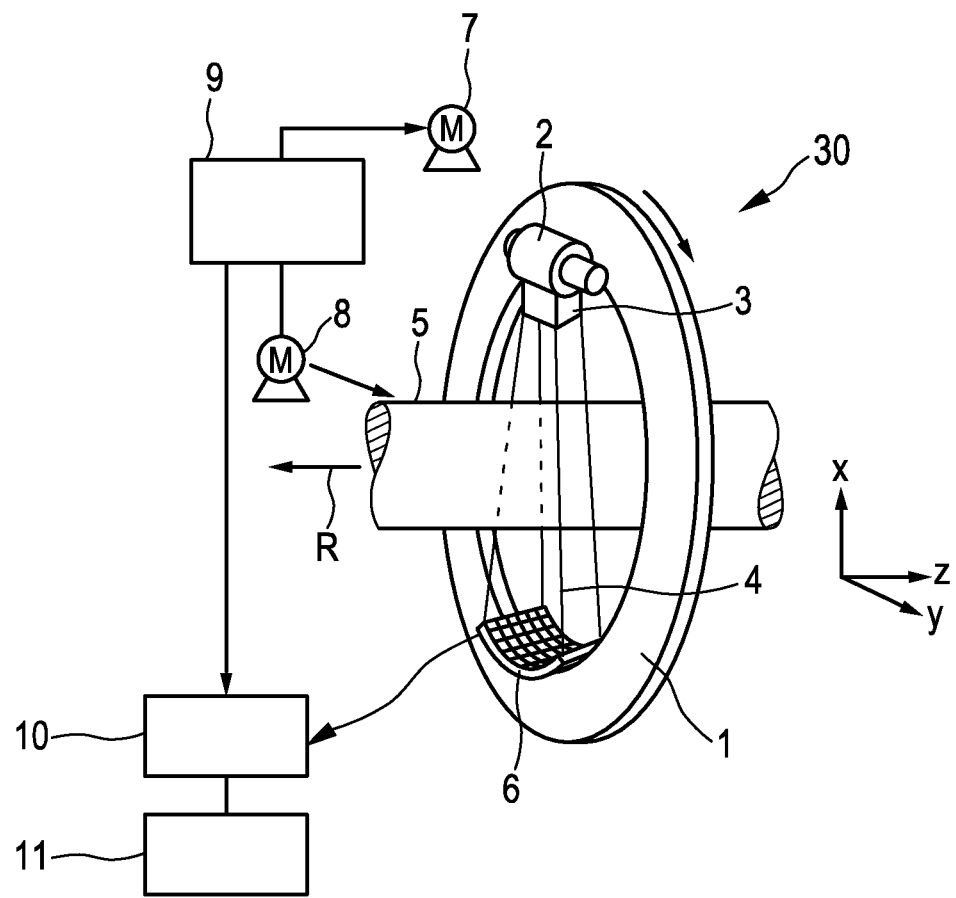
FIG. 1 shows schematically and exemplarily an embodiment of an imaging system for imaging an object.

FIG. 1 shows schematically and exemplarily an imaging system for imaging a region of interest being a computed tomography system 30. The computed tomography system includes a gantry 1 which is capable of rotation about a rotational axis R which extends parallel to the z direction. A radiation source 2, which is, in this embodiment, an x-ray tube, is mounted on the gantry 1. The radiation source 2, which generates polychromatic radiation, is provided with a collimator 3, which forms, in this embodiment, a conical radiation beam 4 from the radiation generated by the radiation source 2. The radiation traverses an object such as a patient in an examination zone 5, which is, in this embodiment, cylindrical. After having traversed the examination zone 5, the radiation beam 4 is incident on a detection apparatus 6, which comprises a two-dimensional detection surface. The detection apparatus 6 is mounted on the gantry 1.

The computed tomography system 30 comprises two motors 7, 8. The gantry 1 is driven at a preferably constant but adjustable angular speed by the motor 7. The motor 8 is provided for displacing the object, for example, a patient, who is arranged on a patient table in the examination zone 5, parallel to the direction of the rotational axis R or the z axis. These motors 7, 8 are controlled by a control unit 9, for instance, such that the radiation source 2 and the examination zone 5, in particular, the object within the examination zone 5, are moved relative to each other along a helical trajectory. However, it is also possible that the object is not moved, but that only the radiation source 2 is rotated, i.e. that the radiation source 2 moves along a circular trajectory relative to the examination zone 5, in particular, relative to the object. Furthermore, in another embodiment, the collimator 3 can be adapted for forming another beam shape, in particular, a fan beam, and the detection apparatus 6 can comprise a detection surface, which is shaped corresponding to the other beam shape, in particular, corresponding to the fan beam.

During a relative movement of the radiation source 2 and the object within the examination zone 5, the radiation source alternatingly switches the generated radiation such that alternatingly radiation having different mean energies traverse the object and are detected by the detection apparatus 6. Thus, two sets of detection values are generated, which correspond to two different mean energies, i.e. energy-resolved detection values being, in this embodiment, projection data are generated.

In the following the detection apparatus 6 will be described in more detail with reference to FIG. 2.

Figure 2:
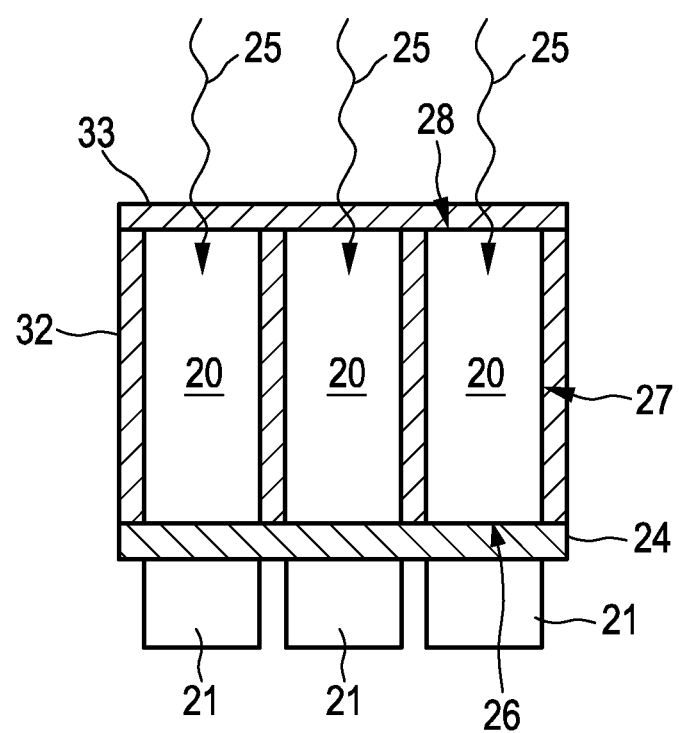
FIGS. 2 and 3 illustrate schematically and exemplarily embodiments of a detection apparatus usable by the imaging system shown in FIG. 1.

FIG. 2 shows schematically and exemplarily a cross section through a part of the detection apparatus. The detection apparatus comprises an array of detection pixels, wherein each detection pixel comprises a GOS element 20 for generating light depending on detected radiation 25 and a detection unit 21 for detecting the scintillation light generated in the respective GOS element. The detection unit 21 is preferentially a photodiode. Each GOS element comprises a radiation entering surface 28, through which the x-ray radiation 25 enters the respective GOS element 20, a scintillation light leaving surface 26 facing the respective detection unit 21 and side surfaces 27 connecting the respective radiation entering surface 28 and the respective scintillation light leaving surface 26. Reflecting elements 32, 33 are provided on the radiation entering surface 28 and the side surfaces 27 for preventing scintillation light from leaving the scintillation light into a neighboring GOS element 20 or into the examination zone 5. The reflecting elements can be made of, for example, $TiO_2$. Between the detection units 21 and the GOS elements 20 an optical filter 24 is arranged, wherein the optical filter 24 is adapted to reduce the intensity of scintillation light having a wavelength being larger than 650 nm. In this embodiment, the optical filter 24 is adapted to block the intensity of scintillation light having a wavelength being larger than 650 nm. The optical filter 24 can be a band pass filter being adapted such that scintillation light having a wavelength within a range of 450 to 650 nm transmits the optical filter. The optical filter can be an optical absorption filter or an interference filter.

Figure 3:
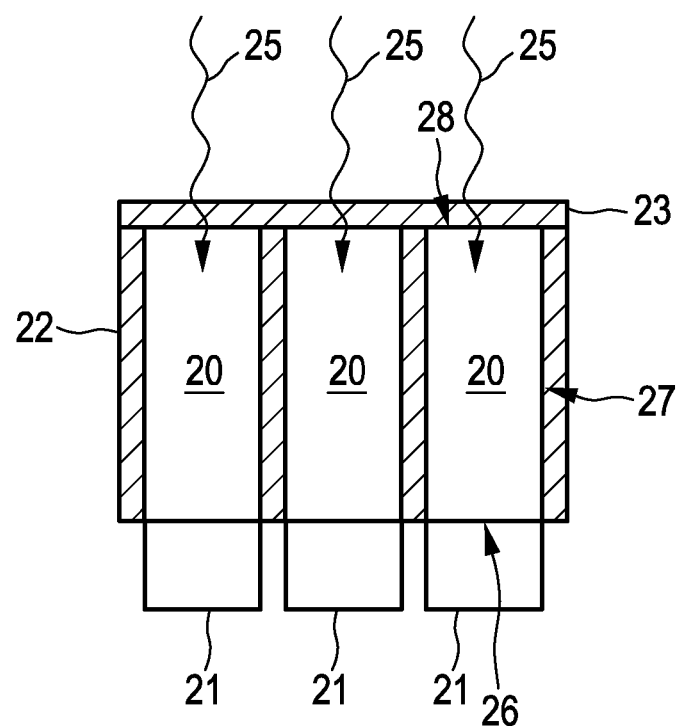

FIG. 3 schematically and exemplarily illustrates a further embodiment of a detection apparatus. The detection apparatus shown in FIG. 3 is similar to the detection apparatus shown in FIG. 2, except for the optical filter and the reflecting elements. In particular, the detection apparatus shown in FIG. 3 does not comprise an optical filter between the GOS elements 20 and the photodiodes 21. Instead, the reflecting elements 22, 23 are adapted to also optically filter the scintillation light such that scintillation light having a wavelength being larger than 650 nm is reduced. The reflecting elements 22, 23 can therefore be regarded as being optical filters arranged on the radiation entering surfaces 28 and the side surfaces 27 of the GOS elements 20. Preferentially, the optical filters/reflecting elements 22, 23 are reflective to scintillation light having a wavelength being smaller than 650 nm and adapted to absorb light having a wavelength being larger than 650 nm.

The optical filter can be a non-scattering filter or a scattering filter. If the optical filter is arranged between the GOS material and the detection unit, the optical filter is preferentially a non-scattering filter. The non-scattering filter can be an interference filter or a non-scattering absorption filter, which can be realized, for example, by applying thin films of organic dyes dispersed in a polymer or a resin. If the optical filter is arranged such that the scintillation light does not pass through the optical filter before being detected by the detection unit, for example, because the optical filter is arranged on the side surfaces and optionally the radiation entering surface, the optical filter is preferentially a scattering or non-scattering optical absorption filter.

In an embodiment, an absorption filter can be used, which is known from liquid crystal displays or from image sensor elements. Alternatively, the absorption filter can comprise red absorbing dye materials as developed for lasers. Such a red absorbing dye material is, for example, Rhodamine 800. Preferentially, the concentration of the red absorbing dye material is high enough to result in concentration quenching of the emission resulting from the absorption of the red scintillation light. In an embodiment, the absorption filter comprises a concentration of the red absorbing dye material being larger than 20 percent by weight.

The interference filter preferentially consists of layers of materials with alternating low and high refractive indexes. These alternating materials are, for example, $SiO_2$ and $TiO_2$. The layers are adapted such that the interference filter has a desired filter function. The interference filter can be made, for instance, by evaporation of suitable precursors, can be obtained as stacked thin films and preferentially do not or hardly scatter light.

The energy-resolved detection values, which have been determined for each position of the radiation source 2 relative to the object within the examination zone 5 and for each detection pixel, are provided to a reconstruction unit 10 for reconstructing an image of the object based on the energy-resolved detection values. The image reconstructed by the reconstruction unit 10 is provided to a display unit 11 for displaying the reconstructed image.

The control unit 9 is preferentially also adapted to control the radiation source 2, the detection apparatus 6 and the reconstruction unit 10.

The reconstruction unit 10 is preferentially adapted to decompose the energy-resolved detection values into different component detection values, which correspond to different components of the object. These different components are, for example, related to different physical effects like the Compton effect and the photoelectric effect and/or the different components can be related to different materials like bone, soft tissue, et cetera of a human being. For instance, the reconstruction unit 10 can be adapted to use the decomposition technique disclosed in the article "Energy-selective reconstructions in X-ray computerized tomography" by R. E. Alvarez et al., Physics in Medicine and Biology, volume 21, number 5, pages 733 to 744 (1976), which is herewith incorporated by reference.

The decomposed detection values are, in this embodiment, decomposed projection data, which can each be used for reconstructing a computed tomography image of the object such that, for instance, for each component a component image of the object can be reconstructed. For instance, a Compton component image and a photoelectric component image can be reconstructed. For reconstructing an image based on the decomposed projection data known reconstruction techniques can be used like a filtered back projection, a Radon inversion, et cetera.

Figure 4:
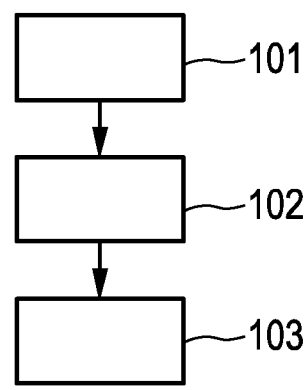
FIG. 4 shows a flowchart exemplarily illustrating an embodiment of an imaging method for imaging an object.

In the following an embodiment of an imaging method for imaging an object will exemplarily be described with reference to a flowchart shown in FIG. 4.

In step 101, the radiation source 2 generates alternatingly radiation having different mean energies. In particular, the radiation source is an x-ray source which is kVp switched between two different kVp values. The radiation is alternatingly generated, while the radiation source 2 and the object are moved relative to each other, in order to allow the radiation to traverse the object in different directions. In particular, the radiation source 2 is moved along a circular or helical trajectory around the object, while the GOS elements 20 generate scintillation light depending on the radiation, the optical filter reduces the intensity of a part of the scintillation light having a wavelength being larger than 650 nm, in particular, substantially completely blocks this part, and the detection units 21 detect the filtered scintillation light.

In step 102, the detection values, which have been determined for each spatial position of the radiation source relative to the object and for each detection pixel, are provided to the reconstruction unit, and an image of the object is reconstructed based on the detection values by using, for example, a computed tomography reconstruction algorithm like a filtered back protection algorithm. In step 103, the reconstructed image is shown on the display unit.

Figure 5:
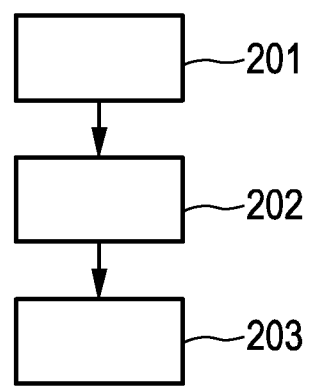
FIG. 5 shows a flowchart exemplarily illustrating an embodiment of a detection method for detecting radiation.

The generation of the detection values described above with reference to step 101 can be regarded as being performed by a detection method for detecting radiation, which will in the following be exemplarily described with reference to a flowchart shown in FIG. 5.

In step 201, scintillation light is generated depending on the radiation, which has been generated by the radiation source and which has traversed the object, by the GOS elements of the detection pixels. In step 202, the intensity of a part of the scintillation light having a wavelength being larger than 650 nm is reduced by the optical filter, and, in step 203, the generated scintillation light, which has been filtered, is detected by the detection unit of the respective detection pixel, wherein each detection unit generates a detection value being indicative of the detected scintillation light.

The GOS material has several emission lines. The fastest emission line is in the green part of the spectrum and has a decay time of about 3.4 μs, but about 25% of the intensity is in a slowly decaying red emission line having a decay time of about 270 μs. This reduces the applicability of GOS elements for fast kVp switching applications, whereby the mean x-ray energy is switched with a frequency of, for instance, 50 to 100 kHz. However, by using an optical filter, for example, an interference filter or a filter based on optical absorption, that removes the slowly decaying red emission line from the luminescence of the GOS elements under x-ray excitation, for example, as described above with reference to FIG. 2, the temporal resolution of the GOS elements is increased such that it is suitable for being used with a kVp switching computed tomography system.

In order to increase the light output of the GOS material, the transparency of the GOS arrays can be enhanced by suitable processing technologies. For instance, the amount of doping, in particular, the amount of $Ce^{3+}$, can be reduced, in order to improve the scintillation light yield.

If the optical filter is an interference filter, the scintillation light having a wavelength being larger than 650 nm does not need to be necessarily lost and can, in an embodiment, still be used when the respective imaging system is operated in a regular integrating mode in which the generated detection values are not energy-resolved. In addition to and perpendicular to the photodiode array for detecting the filtered scintillation light, a further photodiode array can be provided, which is arranged such that the red emission light, i.e. the red scintillation light, reflected by the optical filter is guided to the further photodiode array, which may be parallel to the sides of the GOS scintillator ceramics, i.e. parallel to the GOS element.

The detection apparatuses described above with reference to FIGS. 2 and 3 can have several advantages. For instance, the detection apparatuses can have an improved temporal resolution. Moreover, the generation of the radiation having the larger mean energy of, for instance, 140 kVp is generally more effective than the generation of the radiation having the lower mean energy which corresponds, for example, to 80 kVp. The intensity of the radiation having the larger mean energy is therefore generally larger than the intensity of the radiation having the smaller mean energy before traversing the object. Moreover, since the radiation having the larger mean energy is harder than the other radiation, the radiation having the larger mean energy is less attenuated within the object than the other radiation having the smaller mean energy. The intensity of the radiation having the larger mean energy, which is detected by the detection unit, is therefore much larger, for instance, 100 times larger, than the intensity of the radiation having the smaller mean energy. The detection of these quite different intensities of the radiations is hampered by the relatively slow reaction time of the GOS material, i.e. the radiation is not immediately transformed into scintillation light, but after a relaxation from excited states to ground states after random times, which are described by the exponential law of decay. Since the green scintillation light is emitted relatively fast, whereas the red scintillation light with a wavelength being larger than 650 nm is emitted relatively slow with a decay time of about 270 μs, which is in the same order than the integration time, i.e. of the temporal length of a projection, the red scintillation light will generally be spread into later projections, where the red scintillation light is measured. If kVp switching is used, the intensity of a, for instance, 140 kVp projection, which is spread into a next 80 kVp interval, can be significantly larger than the intensity which is generated by the 80 kVp radiation. The resulting adverse effect on the quality of the generated detection values can be reduced, in particular, eliminated, by using the detection apparatuses having the optical filters as described above with reference to FIGS. 2 and 3.

Furthermore, within the GOS material the part of the scintillation light having a wavelength being larger than 650 nm can be scattered less than the part of the scintillation light having a wavelength being smaller than 650 nm, in particular, than the part of the scintillation light within the wavelength range from 450 nm to 650 nm. Moreover, the part of the scintillation light having a wavelength being smaller than 650 nm may be absorbed stronger by the GOS material in particular due to a presence of $Ce^{3+}$, in particular, for reducing afterglow, which can induce optical absorption in the blue-green region up to some 520 nm and the different absorption cross-sections of the optical transitions on $Pr^{3+}$, which may also be present, at shorter and longer wavelengths. This can result in an uncontrollable ratio of the different parts of the scintillation light having the different wavelengths, because the part of the scintillation light having a wavelength being smaller than 650 nm can be absorbed differently depending on the effective path within the GOS material. Also this effect can be reduced, in particular, eliminated, by the detection apparatuses comprising the optical filters as described above with reference to FIGS. 2 and 3.

Moreover, especially the detection apparatus described above with reference to FIG. 2 can be manufactured by using a pick-and-place detector manufacturing method, wherein the GOS elements 20 are separately adhered to the detection unit array with the detection units 21.

The optical filter described above with reference to FIG. 2 can be adhered to the GOS ceramic scintillator, i.e. to the GOS elements, but it can also be placed on top of the array of detection units.

Although in the embodiment described above with reference to FIG. 2 several GOS elements 20 are attached to the same optical filter 24, in other embodiments each detection pixel can comprise a separate optical filter, which is arranged between the GOS element and the detection unit of the respective detection pixel.

In an embodiment, the detection apparatus can be regarded as being a combination of the detection apparatuses described above with reference to FIGS. 2 and 3. Thus, an optical filter can be arranged between the GOS elements and the detection units and on the radiation entering surface and/or the side surfaces optical elements can be provided, which are reflective to scintillation light having a wavelength being smaller than 650 nm and being adapted to absorb light having a wavelength being larger than 650 nm.

Although in the above described embodiments the radiation source switches between two different radiations having two different mean energies, in other embodiments the radiation source can also be adapted to switch between more alternating kinds of radiation having different mean energies, wherein the detection apparatus is correspondingly adapted to generate detection values for the different kinds of radiation, thereby generating energy-resolved detection values.

Although in the above described embodiments the detection apparatus has been described as being adapted for being used in a computed tomography system, in other embodiments the detection apparatus can also be adapted for being used in other imaging systems like nuclear imaging systems, for instance, single photon emission computed tomography or positron emission tomography imaging systems, or x-ray C-arm imaging systems.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The control of the imaging system in accordance with the imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A detection apparatus for detecting radiation, the detection apparatus comprising:
   a GOS material for generating scintillation light depending on the detected radiation,
   an optical filter for reducing the intensity of all of the scintillation light having a wavelength being larger than 650 nm, wherein the optical filter is reflective to scintillation light having a wavelength being smaller than 650 nm and adapted to absorb light having a wavelength being larger than 650 nm, wherein the optical filter is arranged such that the scintillation light is reflected into the GOS material, and
   a detection unit for detecting the filtered scintillation light.

2. The detection apparatus as defined in claim 1, wherein the optical filter is arranged between the GOS material and the detection unit.

3. The detection apparatus as defined in claim 2, wherein the optical filter is a non-scattering filter.

4. The detection apparatus as defined in claim 1, wherein the optical filter is a band pass filter being adapted such that scintillation light having a wavelength within a range of 450 and 650 nm transmits the optical filter.

5. The detection apparatus as defined in claim 1, wherein the optical filter is an optical absorption filter.

6. The detection apparatus as defined in claim 1, wherein the optical filter is an interference filter.

7. The detection apparatus as defined in claim 1, wherein the detection apparatus comprises an array of detection pixels, wherein each pixel comprises the GOS material and the detection unit, wherein the optical filter is arranged on a surface of the GOS material not facing the detection unit.

8. The detection apparatus as defined in claim 1, wherein the GOS material comprises a radiation entering surface, a scintillation light leaving surface facing the detection unit and side surfaces connecting the radiation entering surface and the scintillation light leaving surface, wherein the optical filter is arranged on at least one of the radiation entering and side surfaces.

9. The detection apparatus as defined in claim 8, wherein the optical filter is arranged on the radiation entering surface and all side surfaces.

10. The detection apparatus as defined in claim 1, wherein the optical filter is an optical absorption filter.

11. An imaging system for imaging an object, the imaging system comprising:
    a radiation source for generating radiation for traversing the object,
    a detection apparatus for detecting the radiation, after having traversed the object, as defined in claim 1 for generating an image of the object.

12. The imaging system as defined in claim 11, wherein the imaging system further comprises a reconstruction unit for reconstructing an image of the object based on the detected radiation.

13. A detection method for detecting radiation, the detection method comprising:
    generating scintillation light depending on the detected radiation by a GOS material,
    reducing the intensity of all of the scintillation light having a wavelength being larger than 650 nm by an optical filter, wherein the optical filter is reflective to scintillation light having a wavelength being smaller than 650 nm and adapted to absorb light having a wavelength being larger than 650 nm, wherein the optical filter is arranged such that the scintillation light is reflected into the GOS material,
    detecting the filtered scintillation light by a detection unit.

14. An imaging method for imaging an object, the imaging method comprising:
    generating radiation for traversing the object by a radiation source,
    detecting the radiation, after having traversed the object, as defined in claim 13, for generating an image of the object.

* * * * *